US012630683B2

(12) United States Patent
Hsu et al.

(10) Patent No.: US 12,630,683 B2
(45) Date of Patent: May 19, 2026

(54) MEDICAL DEVICE WITH TUNABLE HYDROPHOBICITY AND METHOD OF MANUFACTURE

(71) Applicant: BOSTON SCIENTIFIC SCIMED, INC., Maple Grove, MN (US)

(72) Inventors: Yen-Hao Hsu, Shrewsbury, MA (US); Joseph Thomas Delaney, Jr., Minneapolis, MN (US); Paul Vincent Grosso, Maple Grove, MN (US); Patrick Willoughby, Shoreview, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 354 days.

(21) Appl. No.: 18/221,595

(22) Filed: Jul. 13, 2023

(65) Prior Publication Data

US 2024/0043643 A1 Feb. 8, 2024

Related U.S. Application Data

(60) Provisional application No. 63/389,103, filed on Jul. 14, 2022.

(51) Int. Cl.

| | |
|---|---|
| ***C08J 7/12*** | (2006.01) |
| ***A61L 31/10*** | (2006.01) |
| ***B32B 27/40*** | (2006.01) |

(52) U.S. Cl.

CPC ................ *C08J 7/12* (2013.01); *A61L 31/10* (2013.01); *B32B 27/40* (2013.01);

(Continued)

(58) Field of Classification Search

CPC ......... C08J 7/12; C08J 2375/14; A61L 31/10; A61L 29/06; A61L 31/06; A61L 27/18;

(Continued)

(56) References Cited

U.S. PATENT DOCUMENTS

2016/0296323 A1 10/2016 Wulfman et al.
2019/0218334 A1 7/2019 Delaney, Jr. et al.

(Continued)

FOREIGN PATENT DOCUMENTS

WO 2020212978 A1 10/2020
WO 2022010288 A1 1/2022

OTHER PUBLICATIONS

Shu et al., "Attachment and Spreading of Fibrolasts on an RGD Peptide-Modified Injectable Hyaluronan Hydrogel," © 2003 Wiley Periodicals, Inc. J Biomed Mater Res vol. 68A, pp. 365-375, 2004.

(Continued)

*Primary Examiner* — Blaine Copenheaver

(74) *Attorney, Agent, or Firm* — Seager, Tufte & Wickhem, LLP

(57) ABSTRACT

A medical device include a polyurethane layer and a hydro-specific layer that is covalently bonded to the polyurethane layer. The polyurethane layer may include a plurality of monomer residues, at least some of which include pendent alkene groups. The hydro-specific layer may be a hydrophilic layer or a hydrophobic layer depending on the specific molecules used to form the hydro-specific layer. As an example, the hydro-specific layer may be covalently bonded to the polyurethane layer via a thiol-ene or alkene hydrothiolation reaction between the plurality of pendent alkene groups and a plurality of thiol-terminated hydro-specific molecules forming the hydro-specific layer.

17 Claims, 2 Drawing Sheets

(52) U.S. Cl.
CPC ..... *B32B 2307/728* (2013.01); *B32B 2307/73* (2013.01); *C08J 2375/14* (2013.01)

(58) Field of Classification Search
CPC ................. A61L 2400/10; B32B 27/40; B32B 2307/728; B32B 2307/73; C08L 75/04
See application file for complete search history.

(56) References Cited

U.S. PATENT DOCUMENTS

| | | | | |
|---|---|---|---|---|
| 2021/0260256 | A1 | 8/2021 | Boodagh et al. | |
| 2023/0257507 | A1* | 8/2023 | Shin | C08G 18/758<br>525/90 |

OTHER PUBLICATIONS

Zander et al., "Antimicrobial and Antifouling Strategies for Polymeric Medical Devices," ACS Macro Letters, vol. 7 pp. 16-25, 2018.
Zander et al., "Post-Fabrication QAC-Functionalized Thermoplastic Polyurethane for Contact-Killing Catheter Applications," Biomaterials, vol. 178, pp. 339-350, 2018.
International Search Report and Written Opinion dated Nov. 10, 2023 for International Application No. PCT/US2023/027651.
Alibeik et al., "The effect of thiolation on the mechanical and protein adsorption properties of plyurethanes," European Polymer Journal, 43, pp. 1415-1427, 2007.
Hoyle et al., "Thiol-Ene Click Chemistry," Angew. Chem. Int. Ed., 49, pp. 1540-1573, 2010.

* cited by examiner

MEDICAL DEVICE WITH TUNABLE HYDROPHOBICITY AND METHOD OF MANUFACTURE

CROSS-REFERENCE TO RELATED APPLICATIONS

This application claims the benefit of priority of U.S. Provisional Application No. 63/389,103 filed Jul. 14, 2022, the entire disclosure of which is hereby incorporated by reference.

TECHNICAL FIELD

The present disclosure pertains to medical devices and methods for manufacturing medical devices. More particularly, the present disclosure pertains to medical devices and methods for manufacturing medical devices having a tunable hydrophobicity.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. There is an ongoing need to provide alternative medical devices as well as alternative methods for manufacturing and/or using medical devices.

SUMMARY

The disclosure pertains to medical devices and methods for manufacturing medical devices having a tunable hydrophobicity. An example may be found in a medical device that includes a polyurethane layer having a plurality of monomer residues at least some of which include pendent alkene groups, and a hydro-specific layer that is covalently bonded to the polyurethane layer via a thiol-ene reaction between the plurality of pendent alkene groups and a plurality of thiol-terminated hydro-specific molecules forming the hydro-specific layer.

Alternatively or additionally, the monomer residue including a pendent alkene group may include a chain extender molecule residue.

Alternatively or additionally, the chain extender molecule may include a residue of one or more of:

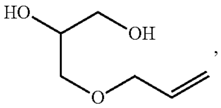
,
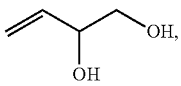

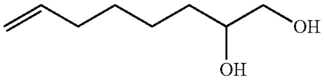
or

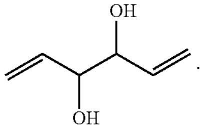

Alternatively or additionally, the chain extender molecule may include a residue of:

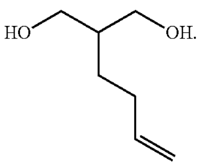

Alternatively or additionally, the hydro-specific layer may include a hydrophilic layer.

Alternatively or additionally, the hydrophilic layer may be formed from a plurality of thiol-terminated hydro-specific molecules comprising one or more of:

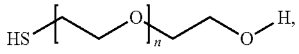

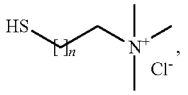

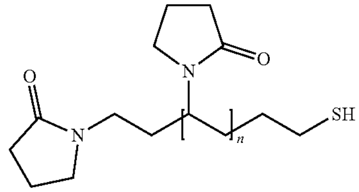
or

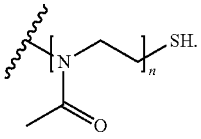

Alternatively or additionally, the hydro-specific layer may include a hydrophobic layer.

Alternatively or additionally, the hydrophobic layer may be formed from a plurality of thiol-terminated hydro-specific molecules comprising one or more of:

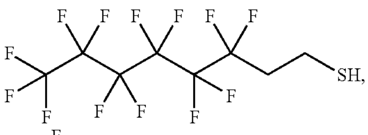

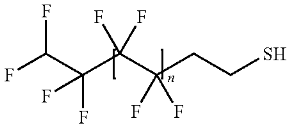
or

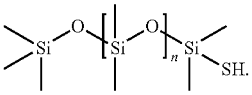

Alternatively or additionally, the medical device may include a first region and a second region, with the polyurethane layer extending through the first region and the second region, and the hydro-specific layer may include a first hydro-specific layer within the first region covalently bonded to the polyurethane layer and a second hydro-specific layer, different from the first hydro-specific layer, disposed within the second region covalently bonded to the polyurethane layer.

Alternatively or additionally, the first hydro-specific layer may include a hydrophilic layer and the second hydro-specific layer may include a hydrophobic layer.

Another example may be found in a medical device having a first region and a second region. The medical device includes a polyurethane layer including a plurality of monomer residues at least some of which include pendent alkene groups, the polyurethane layer extending through the first region and the second region. A first hydro-specific layer is covalently bonded to the polyurethane layer within the first region. A second hydro-specific layer is covalently bonded to the polyurethane layer within the second region.

Alternatively or additionally, the first hydro-specific layer may provide a first contact angle and the second hydro-specific contact angle may provide a second contact angle different from the first contact angle.

Alternatively or additionally, the first hydro-specific layer may provide a contact angle of less than or equal to 90 degrees.

Alternatively or additionally, the second hydro-specific layer may provide a contact angle of greater than 90 degrees.

Alternatively or additionally, the first hydro-specific layer may be covalently bonded to the polyurethane layer via a thiol-ene reaction between the plurality of pendent alkene groups and a plurality of thiol-terminated hydro-specific molecules forming the first hydro-specific layer.

Alternatively or additionally, the second hydro-specific layer may be covalently bonded to the polyurethane layer via a thiol-ene reaction between the plurality of pendent alkene groups and a plurality of thiol-terminated hydro-specific molecules forming the second hydro-specific layer.

Another example may be found in a medical device that includes a polyurethane layer formed to include a plurality of pendent functional chemical handles and a hydro-specific layer that is covalently bonded to the polyurethane layer, the second layer including a plurality of hydro-specific molecules covalently bonded to the plurality of pendent functional chemical handles.

Alternatively or additionally, the plurality of pendent functional chemical handles may include a plurality of pendant alkene groups.

Alternatively or additionally, the plurality of hydro-specific molecules may include thiol-terminated hydro-specific molecules.

Alternatively or additionally, the hydro-specific layer may be covalently bonded to the polyurethane layer via an alkene hydrothiolation reaction between the plurality of pendant alkene groups and the thiol-terminated hydro-specific molecules.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
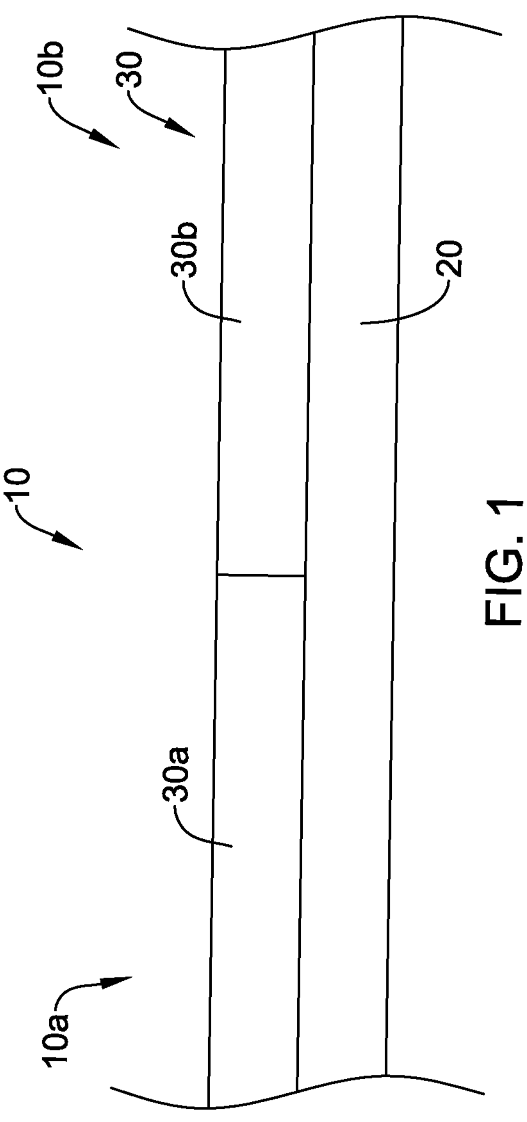
FIG. 1 is a schematic view of a portion of an illustrative medical device having a polyurethane layer and a hydro-specific layer covalently bonded to the polyurethane layer.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

FIG. 1 is a highly schematic view of a portion of an illustrative medical device 10. The illustrative medical device 10 may represent part of a medical device having a polymeric structure, such as a catheter, for example. As shown, the medical device 10 includes a first polymeric layer 20 and a second polymeric layer 30. As will be discussed, in some cases the second polymeric layer 30 may be covalently bonded to the first polymeric layer 20. The first polymeric layer 20 may include pendant functional chemical handles that may be used in covalently bonding the second polymeric layer 30 to the first polymeric layer 20.

In some cases, the first polymeric layer 20 may be a polyurethane layer while the second polymeric layer 30 may be a hydro-specific layer. In this, a hydro-specific layer is a layer having a particular or desired or intended hydrophobicity (or hydrophilicity). Put another way, a hydro-specific layer may be a polymeric layer defined by a particular contact angle. In some cases, a surface having a contact angle that is less than or equal to 90 degrees may be considered as being a hydrophilic surface while a surface having a contact angle that is between degrees and 150 degrees may be considered as being a hydrophobic surface. In some cases, a surface having a contact angle of less than 5 degrees may be considered as being a superhydrophilic surface while a surface having a contact angle between 150 and 180 degrees may be considered as being a superhydrophobic surface.

In some cases, the medical device 10 may be considered as including a first region 10*a* and a second region 10*b*. In some cases, the first polymeric layer 20 extends through both the first region 10*a* and the second region 10*b*. In some cases, the second polymeric layer 30 may include a first hydro-specific layer 30*a* that corresponds to the first region 10*a* and a second hydro-specific layer 30*b* that corresponds to the second region 10*b*. As an example, the first hydro-specific layer 30*a* may be hydrophilic while the second hydro-specific layer 30*b* may be hydrophobic. As another example, the first hydro-specific layer 30*a* may be relatively less hydrophilic, perhaps with a contact angle of 75 degrees while the second hydro-specific layer may be relatively more hydrophilic, perhaps with a contact angle of 15 degrees. As another example, the first hydro-specific layer 30*a* may be relatively less hydrophobic, perhaps with a contact angle of 100 degrees, while the second hydro-specific layer 30*b* may be relatively more hydrophobic, perhaps with a contact angle of 135 degrees. These numerical examples are not intended to limit, but merely to illustrate.

Figure 2:
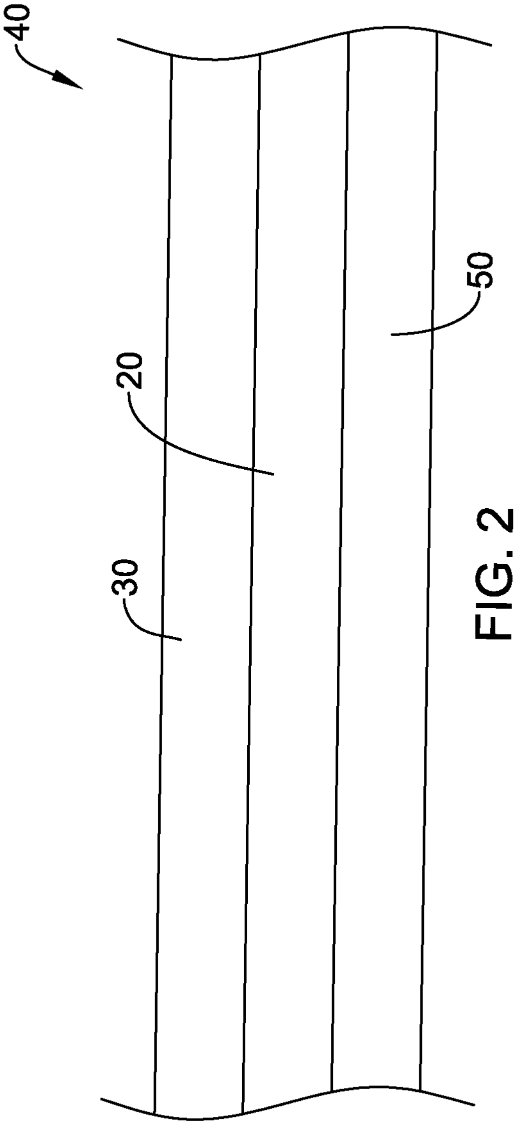
FIG. 2 is a schematic view of a portion of an illustrative medical device including a substrate, a polyurethane layer disposed on the substrate and a hydro-specific layer covalently bonded to the polyurethane layer.

While a total of two polymeric layers 20 and 30 are shown in FIG. 1, it will be appreciated that the medical device 10 may include additional layers, such as one or more additional polymeric layers that form a substrate for the first polymeric layer 20. In some cases, the one or more additional polymeric layers may include reinforcing structures, such as but not limited to braids and coils. In some cases, a medical device may include a substrate that may include polymers and other components. A medical device may include a metallic substrate, for example. FIG. 2 is a highly schematic view of an illustrative medical device 40 that includes the first polymeric layer 20 and the second polymeric layer 30, but also includes a substrate 50.

The illustrative medical device 40 may represent part of a guidewire, and the substrate 50 may represent a part of the metal structure of the guidewire. The illustrative medical device 40 may represent part of a stent, and the substrate 50 may represent a part of the expandable framework of the stent. The illustrative medical device 40 may represent part of a left atrial appendage closure (LAAC) device, and the substrate 50 may represent part of the expandable framework of the LAAC device. The illustrative medical device 40 may represent part of a bone pin or a staple, for example. The illustrative medical device 40 may represent a pacemaker lead, which includes conductive elements within polymeric insulators. These are just examples. In some cases, the substrate 50 may be formed of one or more polymers. In some cases, the substrate 50 may be formed of, or may include, one or more metallic materials.

Figure 3:
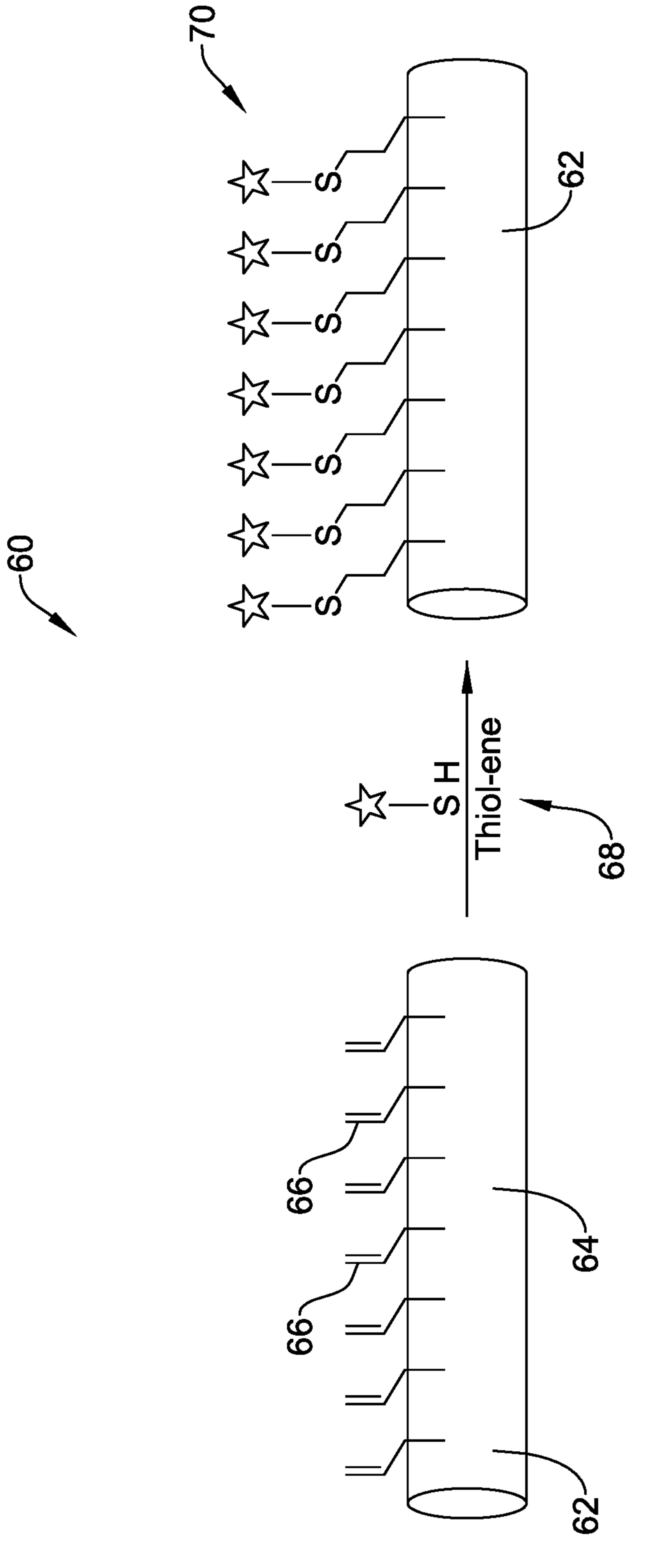
FIG. 3 is a schematic view of an illustrative reaction scheme for forming the illustrative medical device of FIGS. 1 and 2.

FIG. 3 is a schematic view of an illustrative reaction scheme 60 for forming the medical device 10 and the medical device 40. As noted, in some cases the second polymeric layer 30 may be covalently bonded to the first polymeric layer 20. FIG. 3 shows an illustrative medical device 62 that may be considered as being an example of the medical device 10 or the medical device 40. The medical device 62 is schematically shown as being cylindrical or largely cylindrical in shape, but this is not required.

The medical device 62 has an outer surface 64 that in some cases may be a polyurethane layer such as the second polymer layer 30. The polyurethane layer includes a number of functional chemical handles 66 that extend outward from the outer surface 64. In some cases, as shown, the functional chemical handles 66 are pendant alkene groups that may be used in covalently bonding a hydro-specific layer to the medical device 62. In some cases, the hydro-specific layer may be covalently bonded to the functional chemical handles 66, and thus to the outer surface 64 (of the polyurethane layer) via a thiol-ene reaction 68 in which a plurality of thiol-capped hydro-specific molecules are covalently bonded with the pendant alkene groups. The thiol-ene reaction 68 is also known as an alkene hydrothiolation reaction.

As a result, and as shown on the right side of FIG. 3, the medical device 62 now has an outer layer 70 that is hydro-specific. If the thiol-capped hydro-specific molecules are thiol-capped hydrophilic molecules, then the outer layer 70 is hydrophilic. If the thiol-capped hydro-specific molecules are thiol-capped hydrophobic molecules, then the outer layer 70 is hydrophobic.

A polyurethane layer such as the second polymer layer 30, or one forming the outer surface 64, may be formed by polymerizing a polyol with a diisocyanate or polymeric isocyanate in the presence of suitable catalyst and additives. In a particular example, a polyurethane suitable as the second polymer layer 30, or the one forming the outer surface 64, may be formed by polymerizing MDI (methylene diphenyl diisocyanate) with PTMO (polytetramethylene oxide) and a chain extender molecule that includes a pendent alkene group. As shown below, 2-(3-buten-1-yl)-1,3-propane diol is an example of a suitable chain extender molecule having a pendant alkene group:

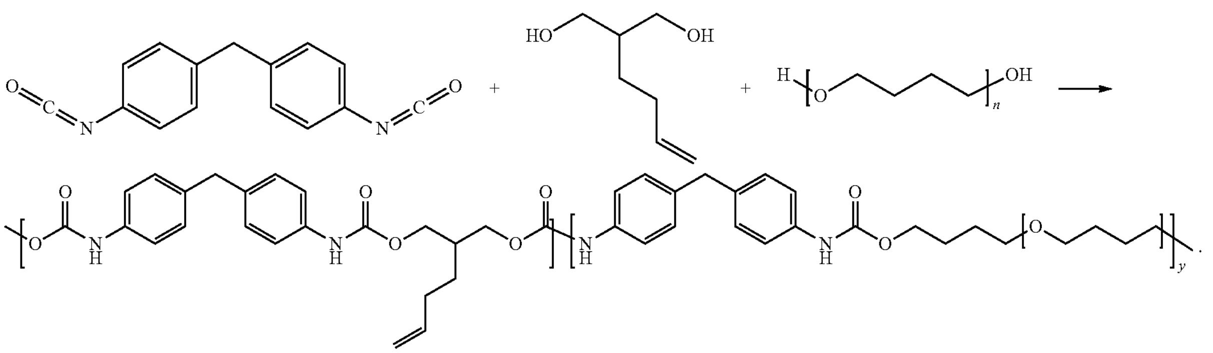

As can be seen, the resulting polyurethane includes the pendant alkene groups that may be used subsequently to covalently bond a desired hydro-specific layer over the polyurethane layer. In some cases, standard polyurethane-forming conditions may be appropriate, such as reacting at room temperature in the presence of a tin-containing catalyst. In some cases, and for 2-(3-buten-1-yl)-1,3-propane diol, a range between 2 and 20% by weight of the polyol component would be appropriate.

As an example, following the reaction shown above, 0.95 equivalent of PTMO and 0.05 equivalent of 2-(3-buten-1-yl)-1,3-propane diol may be combined in a porcelain enamel-lined tin can with overheat mechanical stirring and may be preheated to 100° C. Next, 1 equivalent of HDMI may be added, immediately followed by 2 or 3 drops of stannous octoate catalyst. The mixture may be stirred until the mixture becomes too viscous to stir. The resulting TPU may be oven cured at 100° C. for an additional hour.

It will be appreciated that other diisocyanates may be used in forming the polyurethane. For example, (4,4'-diisocyanato dicyclohexyl methane) (H12MDI) or hexamethylene diisocyanate (HDI) may be used. H12MDI and HDI have the following structures, respectively:

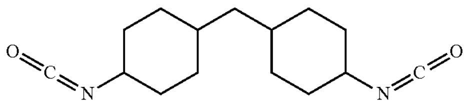

and

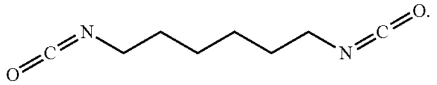

In some cases, the polyurethane may include a soft segment that is formed from one or more of hydroxyl-terminated polybutadiene or hydroxyl-terminated polyisobutylene. These molecules have the following structures, respectively:

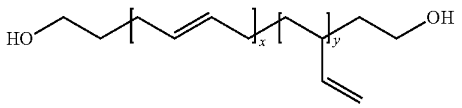

or

-continued

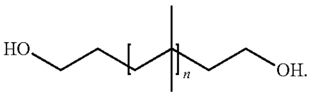

In some cases, a variety of different chain extender molecules may be used. In some cases, as shown above, 2-(3-buten-1-yl)-1,3-propane diol may be used. This molecule has the following structure:

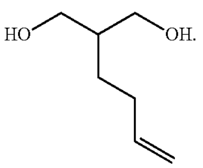

In some cases, the chain extender molecule may be a polyol including one or more pendant alkene groups. In some cases, the chain extender molecule may be selected from one or more of the following. 3-((allyloxy)-1,2-propanediol, 3,4-dihydroxy-1-butane, 7-octen-1,2-diol and 1,5-hexadiene-3,4-diol have the following structures, respectively:

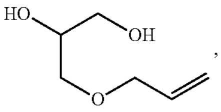,
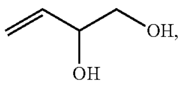

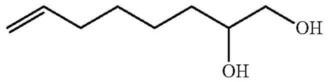 and

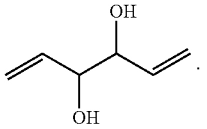

Once the polyurethane layer has been formed, including the pendant alkene groups, a hydro-specific layer such as a hydrophilic layer or a hydrophobic layer may be covalently bonded to the polyurethane layer. If a hydrophilic layer is desired, one of the following thiol-capped hydrophilic molecules may be used. PEG-SH (thiol-terminated polyethylene glycol), quaternary ammonium thiol derivatives, PVP-SH (thiol-terminated polyvinylpyrrolidone) or thiol-terminated poly (2-methyl-2-oxazoline) may be used. These molecules have the following structures, respectively:

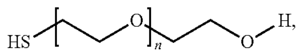

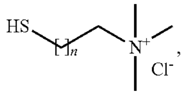

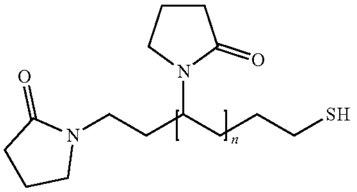 and

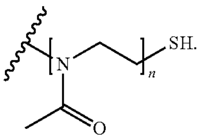

If a hydrophobic layer is desired, one of the following thiol-capped hydrophobic molecules may be used. 2-perfluorohexyl ethyl thiol, PTFE-SH (thiol-terminated polytetrafluoroethylene) or PDMS-SH (thiol-terminated polydimethylsiloxane may be used. These molecules have the following structures, respectively:

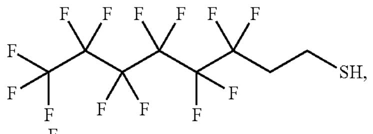

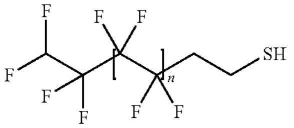 and

-continued

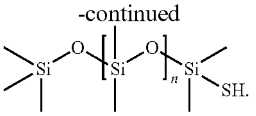

In some cases, thiol-based dye molecules may be added to the polyurethane, either instead of the hydro-specific material or in combination therewith. Suitable thiol-based dye molecules include but are not limited to:

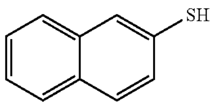

2-Naphthalenethiol (CAS# 91-60-1),

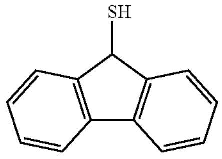

9-Mercaptofluorene (CAS# 19552-08-0),

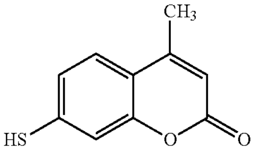

7- Mercapto-4-methylcoumarin (CAS# 137215-27-1), or

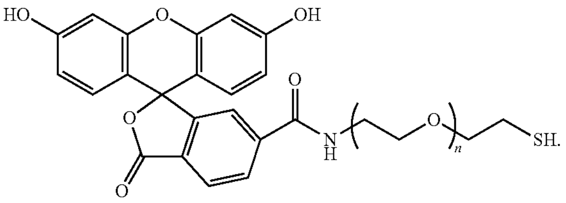

FITC-PEG-SH (https://www.biochempeg.com/product/FITC-PEG-SH.html)

In some cases, certain thiol-terminated RGD (Arg-Gly-Asp) peptide sequences may be attached. RGD peptides include Arginine, Glycine and Aspartate. Adding thiol-terminated RGD peptide sequences may help to bolster cell proliferation in order to help tissue regeneration. Examples of suitable thiol-terminated RGD peptide sequences include but are not limited to the following, in which cysteine (Cys) provides the thiol group:

Cys-Arg-Gly-Asp-Ser (CRGDS),
Cys-Cys-Arg-Gly-Asp-Ser (CCRGDS), and
Cys-Arg-Asp-Gly-Ser (CRDGS).

The materials that can be used for the various components of the medical device systems described herein and the various elements thereof disclosed herein may include those commonly associated with medical devices. In some embodiments, the medical device systems described herein may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; combinations thereof; and the like; or any other suitable material.

In at least some embodiments, portions or all of the medical device systems described herein may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the medical device systems. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device systems described or alluded to herein.

In some embodiments, a degree of Magnetic Resonance Imaging (MM) compatibility is imparted into the medical device systems described herein. The medical devices described herein may be made of a material that does not substantially distort the image and create substantial artifacts (e.g., gaps in the image). Certain ferromagnetic materials, for example, may not be suitable because they may create artifacts in an MRI image. In some cases, the medical device systems, or portions thereof, may also be made from a material that the Mill machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the medical device systems described herein may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex® high-density polyethylene, Marlex® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

In some embodiments, the medical device systems described herein and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical device, comprising:

a polyurethane layer comprising a plurality of monomer residues;

wherein at least some of the plurality of monomer residues include a chain extender molecule with a pendent alkene group;

wherein the chain extender molecule comprises a residue of one or more of:

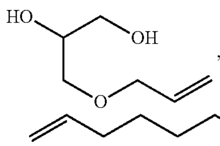
,
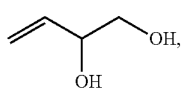

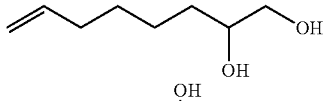
or

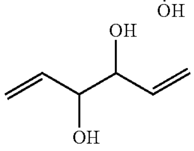
; and a hydro-specific layer covalently bonded to the polyurethane layer via a thiol-ene reaction between the plurality of pendent alkene groups and a plurality of thiol-terminated hydro-specific molecules forming the hydro-specific layer.

2. The medical device of claim 1, wherein the hydro-specific layer comprises a hydrophilic layer.

3. The medical device of claim 2, wherein the hydrophilic layer is formed from a plurality of thiol-terminated hydro-specific molecules comprising one or more of:

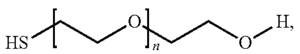

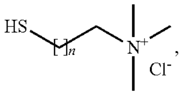

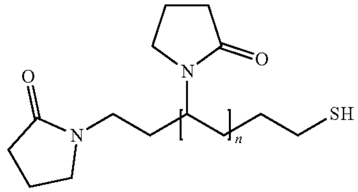 or

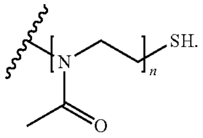

4. The medical device of claim 1, wherein the hydro-specific layer comprises a hydrophobic layer.

5. The medical device of claim 4, wherein the hydrophobic layer is formed from a plurality of thiol-terminated hydro-specific molecules comprising one or more of:

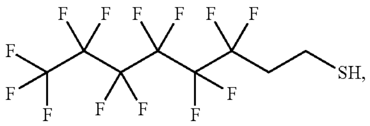

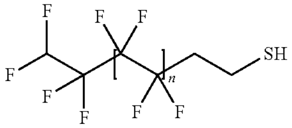 or

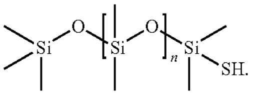

6. The medical device of claim 1, comprising a first region and a second region, with the polyurethane layer extending through the first region and the second region, and the hydro-specific layer comprises a first hydro-specific layer within the first region covalently bonded to the polyurethane layer and a second hydro-specific layer, different from the first hydro-specific layer, disposed within the second region covalently bonded to the polyurethane layer.

7. The medical device of claim 6, wherein the first hydro-specific layer comprises a hydrophilic layer and the second hydro-specific layer comprises a hydrophobic layer.

8. A medical device having a first region and a second region, the medical device comprising:

a polyurethane layer comprising a plurality of monomer residues, the polyurethane layer extending through the first region and the second region;

wherein at least some of the plurality of monomer residues include a chain extender molecule with a pendent alkene group;

wherein the chain extender molecule comprises a residue of one or more of:

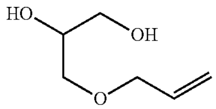 , 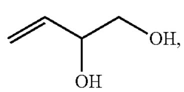

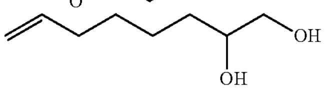 or

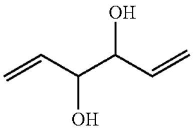 ;

a first hydro-specific layer covalently bonded to the polyurethane layer within the first region; and a second hydro-specific layer covalently bonded to the polyurethane layer within the second region.

9. The medical device of claim 8, wherein the first hydro-specific layer provides a first contact angle and the second hydro-specific contact angle provides a second contact angle different from the first contact angle.

10. The medical device of claim 9, wherein the first hydro-specific layer provides a contact angle of less than or equal to 90 degrees.

11. The medical device of claim 9, wherein the second hydro-specific layer provides a contact angle of greater than 90 degrees.

12. The medical device of claim 8, wherein the first hydro-specific layer is covalently bonded to the polyurethane layer via a thiol-ene reaction between the plurality of pendent alkene groups and a plurality of thiol-terminated hydro-specific molecules forming the first hydro-specific layer.

13. The medical device of claim 8, wherein the second hydro-specific layer is covalently bonded to the polyurethane layer via a thiol-ene reaction between the plurality of pendent alkene groups and a plurality of thiol-terminated hydro-specific molecules forming the second hydro-specific layer.

14. A medical device, comprising:

a polyurethane layer formed to include a plurality of pendent functional chemical handles;

wherein the polyurethane layer include a chain extender molecule having the plurality of pendent functional chemical handles;

wherein the chain extender molecule comprises a residue of one or more of:

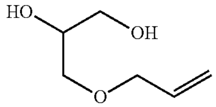 , 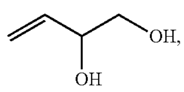

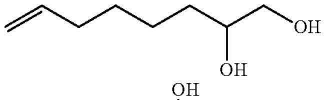 or

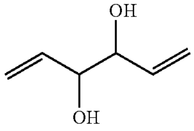 ; and a hydro-specific layer covalently bonded to the polyurethane layer, the hydro-specific layer including a plurality of hydro-specific molecules covalently bonded to the plurality of pendent functional chemical handles.

15. The medical device of claim 14, wherein the plurality of pendent functional chemical handles comprise a plurality of pendant alkene groups.

16. The medical device of claim 15, wherein the plurality of hydro-specific molecules comprise thiol-terminated hydro-specific molecules.

17. The medical device of claim 16, wherein the hydro-specific layer is covalently bonded to the polyurethane layer via an alkene hydrothiolation reaction between the plurality of pendant alkene groups and the thiol-terminated hydro-specific molecules.

* * * * *